United States Patent [19]

Bible et al.

[11] Patent Number: 5,384,543
[45] Date of Patent: Jan. 24, 1995

[54] PORTABLE MICROWAVE INSTRUMENT FOR NON-DESTRUCTIVE EVALUATION OF STRUCTURAL CHARACTERISTICS

[75] Inventors: Don W. Bible, Clinton; Richard I. Crutcher, Knoxville; Carl W. Sohns, Oak Ridge; Stephen R. Maddox, Loudon, all of Tenn.

[73] Assignee: Martin Marietta Energy Systems, Inc., Oak Ridge, Tenn.

[21] Appl. No.: 972,776

[22] Filed: Nov. 9, 1992

[51] Int. Cl.6 .................................................. G01R 27/00
[52] U.S. Cl. ...................................... 324/644; 324/637
[58] Field of Search .............. 324/637, 642, 643, 644; 455/300

[56] References Cited

U.S. PATENT DOCUMENTS

| | | |
|---|---|---|
| 4,482,160 | 12/1969 | Prine . |
| 3,490,037 | 1/1970 | Williams . |
| 3,534,260 | 10/1970 | Walker . |
| 3,562,642 | 2/1971 | Hochschild . |
| 3,810,005 | 5/1974 | Bennion et al. . |
| 4,075,555 | 2/1978 | Wight et al. . |
| 4,344,030 | 8/1982 | Anderson et al. . |
| 4,455,682 | 6/1984 | Masters .................. 455/300 |
| 4,492,915 | 1/1985 | Caspers ................. 324/637 |
| 4,514,680 | 4/1985 | Heikkila et al. . |
| 4,818,930 | 4/1989 | Flemming et al. . |
| 5,068,614 | 11/1991 | Fields et al. ........... 324/644 |
| 5,103,182 | 4/1992 | Moslehi ................. 324/644 |
| 5,177,444 | 1/1993 | Cutmore ................ 324/637 |
| 5,216,372 | 6/1993 | Zoughi et al. ......... 324/644 |

Primary Examiner—Maura K. Regan
Attorney, Agent, or Firm—Edward A. Pennington; Michael S. Marcus; James M. Spicer

[57] ABSTRACT

A portable microwave instrument for evaluating characteristics of a structural member includes a source of microwave energy, a transmitter coupled to the source of microwave energy for transmitting a microwave signal at the structural member, and a receiver positioned on the same side of the structural member as the transmitter and being disposed to receive a microwave signal reflected by the structural member. A phase angle difference is determined between the transmitted microwave signal and the received microwave signal using a signal splitter and a balanced mixer. The difference in phase angle varies in accordance with differences in size, shape and locations of constituent materials within the structural member.

16 Claims, 5 Drawing Sheets

PORTABLE MICROWAVE INSTRUMENT FOR NON-DESTRUCTIVE EVALUATION OF STRUCTURAL CHARACTERISTICS

This invention was made with Government support under contract DE-AC05-84OR21400 awarded by the U.S. Department of Energy to Martin Marietta Energy Systems, Inc. and the Government has certain rights in this invention.

FIELD OF THE INVENTION

The present invention relates generally to non-destructive measuring and testing using microwave energy and, more particularly, to a hand-held, portable instrument capable of evaluating structural members, such as building walls, to determine the characteristics of their construction. The instrument uses low-power microwave energy and differential phase detection to characterize the size of blocks, location of voids, etc., within a wall.

BACKGROUND OF THE INVENTION

Non-destructive evaluation entails various technologies that permit analysis of materials without destroying the object formed of the material. For example, magnetic, ultrasonic, and/or acoustic measuring instruments are used to evaluate metals in a variety of products for latent flaws, cracks, etc., in order to anticipate, and thereby obviate, a part failure.

Civil engineers use non-destructive evaluation for bridge and building inspection. As buildings age, varying amounts of deterioration occur and safety issues such as seismic tolerance become significant. Some structures can be examined by established technologies such as ultrasonics or radiography, but these have serious limitations that make them unsuitable for many situations. One particularly difficult evaluation problem is for buildings having walls constructed of block, terra cotta, and/or other masonry materials where it is not possible to visually determine the exact construction of the wall in terms of the dimensions and orientation of the constituent materials, the presence or absence of voids within the wall, and the presence of different types of materials within the walls.

In situations described above, transmission-type devices, such as radiographic instruments, are limited because one needs access to both sides of the wall. Moreover, radiographic techniques using X-rays or isotope sources are generally slow and require the building to be unoccupied. Access to both sides of the wall, for through-transmission, may not be possible where the wall is a foundation wall, for example.

Ultrasonics are limited by the fact that the transducer must be mounted on a smooth surface.

Capacitive measurements have been used to locate studs within walls, but these have been successful only in determining position of a stud concealed in plaster or drywall.

Infrared thermography can be used to image or map density differences of constituent materials within a wall, but it is difficult to set the imaging camera and requires access to both sides of the wall.

SUMMARY OF THE INVENTION

An object of the present invention is to provide a portable microwave instrument for non-destructive evaluation of structural characteristics which is relatively simple in construction and easy to operate.

Another object of the present invention is to provide a portable microwave instrument for non-destructive evaluation of structural characteristics which is capable of inspecting building walls without physically invading the structure, and without requiring access to both sides of the wall.

These and other objects of the invention are met by providing a portable microwave instrument for evaluating characteristics of a structural member which includes a source of microwave energy, a transmitter coupled to the source of microwave energy for transmitting a microwave signal at the structural member, a receiver positioned on the same side of the structural member as the transmitter and being disposed to receive a microwave signal reflected by the structural member, and means for comparing the phase angle of the transmitted microwave signal to the received microwave signal to determine a difference, said difference varying in accordance with differences in size, shape and locations of constituent materials within the structural member.

Other objects, advantages and salient features of the invention will become apparent from the following detailed description, which taken in conjunction with the annexed drawings, discloses preferred embodiments of the invention.

DETAILED DESCRIPTION OF THE INVENTION

Figure 1:
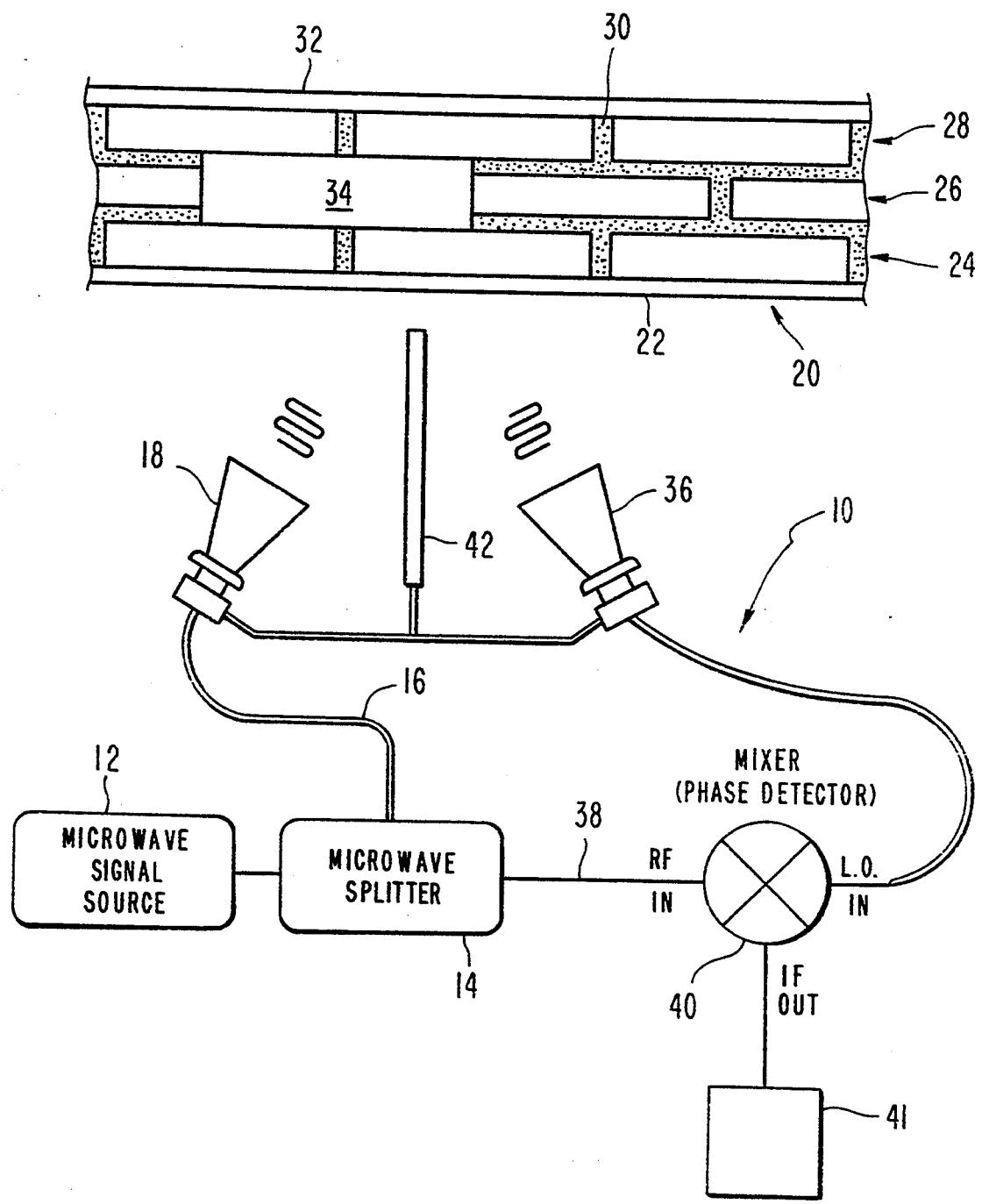
FIG. 1 is a schematic view of a first preferred embodiment of a portable microwave instrument according to the present invention.

Referring to FIG. 1, a portable microwave instrument 10 includes a microwave signal source 12 which generates a microwave signal over a given frequency range which, as will be explained more fully below, can be swept to provide a readable two-dimensional signature between, for example, 7 and 10 GHz.

The signal source feeds the signal to a microwave splitter 14 which functions as a wideband resistive power divider to provide two output signals. One of the two signals is fed through coaxial cable 16 to a transmitter or microwave horn antenna 18 so that the antenna transmits a microwave signal at a structural member 20, which in the illustration of FIG. 1 is a wall having an exposed plaster or drywall layer 22, three rows of masonry block 24, 26, and 28 with mortar 30 in the joints therebetween. An unexposed layer 32 of a different constituent material, such as a sealant, is provided on the side opposite the plaster layer 22. If exposed, layer 32 could be an exterior stucco, concrete or other masonry or non-masonry material.

A void 34 is formed between rows 24 and 28 where a block was omitted during construction. In order to evaluate the composition of the wall 20, for example, in undertaking a seismic analysis of the building within which the wall 20 is a structural member, the evaluator has a general idea of the materials used to construct the wall 20 but will not initially know the size or orientation of the blocks, the presence or absence of voids such as void 34, or the presence or absence of mortar 30 filling voids within individual blocks, such as when cinder blocks are used to construct the wall 20. Evaluation needs to be made without compromising the structural integrity of the wall 20, meaning that a non-destructive evaluation is required.

According to the present invention, this evaluation is performed by measuring phase shift of reflected microwave signals. A receiver 36 is positioned on the same side of the structural member or wall 20 as the transmitter 18 and is disposed to receive a microwave signal reflected by the wall at each boundary or transition between the different constituent material comprising the wall 20.

The other signal from the splitter 14 is delivered through coaxial cable 38 to a balanced mixer 40 (or "phase detector") as a reference signal ("RF IN"). The balanced mixer 40 provides means for comparing the phase angle of the transmitted microwave signal to the received microwave signal to determine a difference. The difference varies in accordance with differences in size, shape and locations of constituent materials within the wall 20. A metal shield 42 prevents crosstalk between the transmitter 18 and the receiver 36, without hindering the signal through the sample, and is interposed therebetween.

The splitter 14 is commercially available. A representative example of a workable splitter is the Model 4232 microwave splitter sold by Sage Laboratories. Similarly, the balanced mixer 40 is commercially available, and a representative workable balanced mixer is the Model M77C sold by Watkins Johnson of Gaithersburg, Md.

The wall constituents reflect a portion of the transmitted microwave energy transmitted by the transmitter 18, and the reflected signals are received by the receiver 36. The received signal is applied to the balanced mixer 40 as the local oscillator input (L.O. IN), along with the reference signal in order to provide phase detection. The output of the balanced mixer 40 is the "intermediate frequency" output (IF OUT) which is a voltage that is proportional to the phase angle between the reference signal and the vector sum of the signals reflected from the wall constituents. This voltage is applied to a display device 41 located on the hand held instrument as an analog value, or the display can include a microprocessor for conducting two dimensional signature analysis in which a sweep frequency produces a two dimensional signature which is compared to stored specimen signatures based on known wall characteristics. Each constituent of the wall produces a unique signature for the identification of the inner wall structure.

Figure 2:
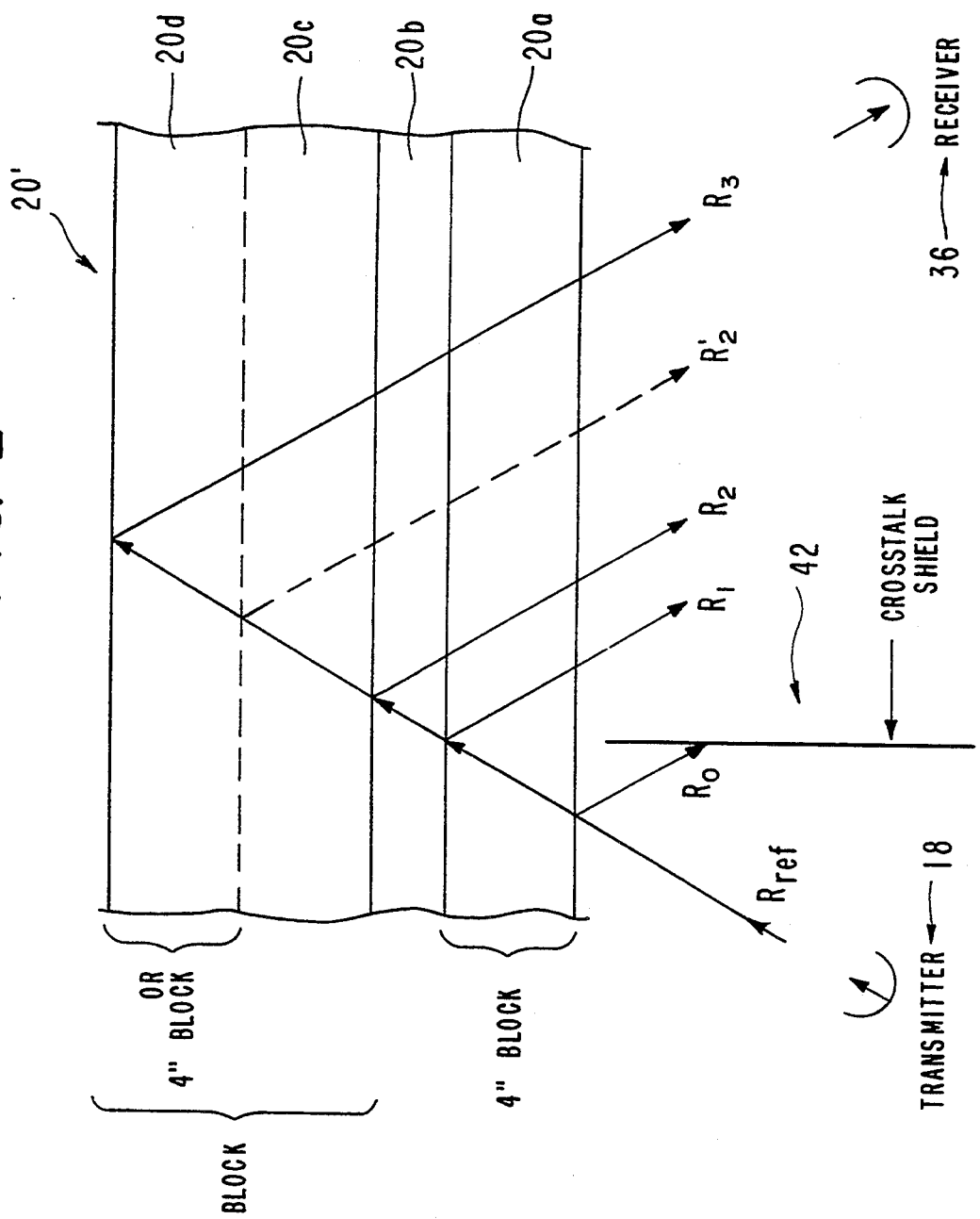
FIG. 2 is a ray diagram illustrating the reflected signals generated by the instrument of FIG. 1.

FIG. 2 is a ray diagram of the RF penetration into the wall. Each air-to-block interface, or transition between materials, creates a division between the portion of the RF energy transmitted and the portion reflected. A wall with multiple faces will generate a primary reflection from each boundary producing a number of different ray lengths. The combination of these reflected signals forms a summation ray that is received by the receiver 36.

Figure 3:
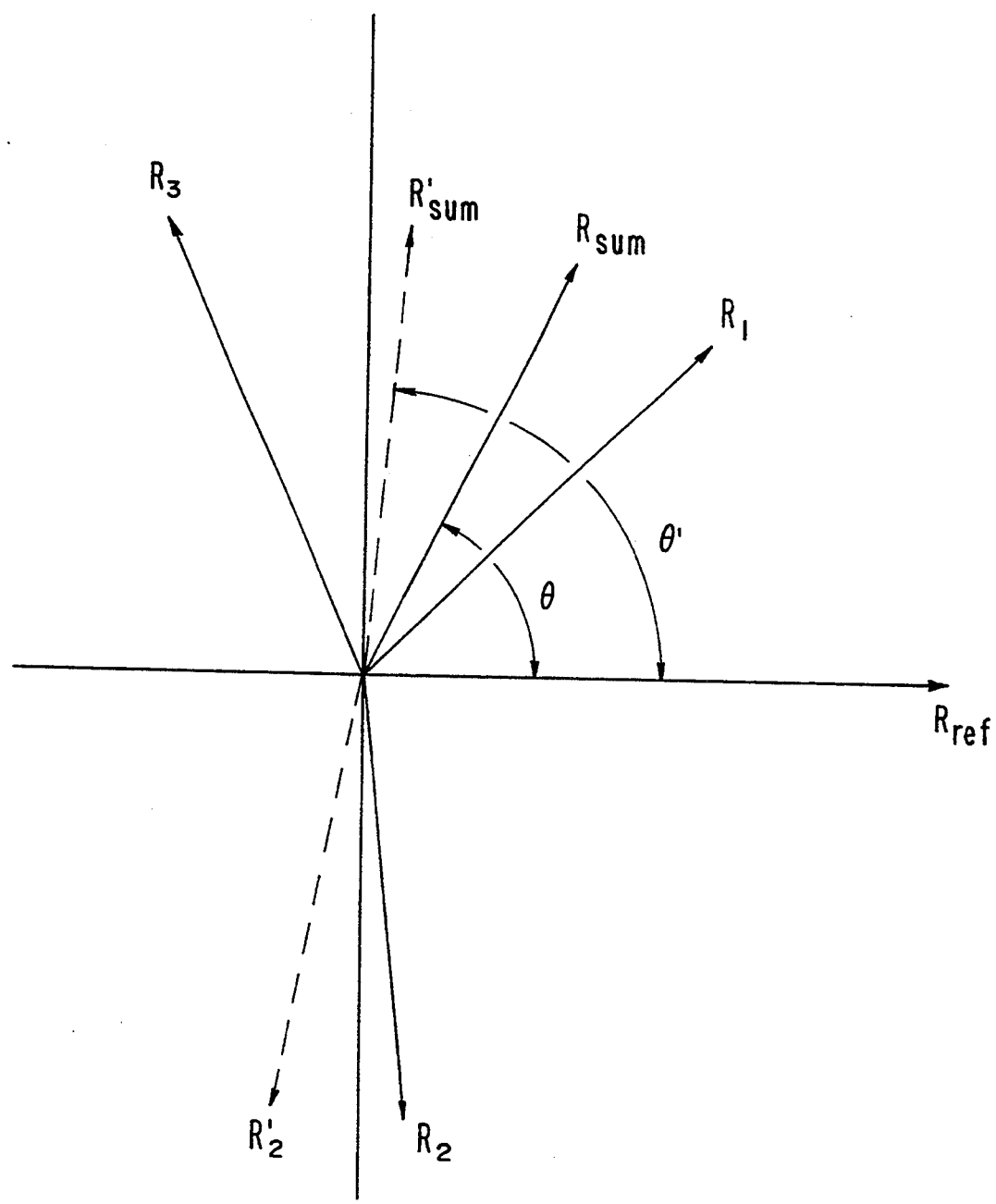
FIG. 3 is a vector summation diagram based on the ray diagram of FIG. 2.

In FIG. 2, the wall 20' to be evaluated according to the present invention is shown having a four inch block 20a, a void 20b, and a twelve inch block 20c (shown in broken line alternatively as a four inch block 20d. Each face produces a reflected signal R0, R1, R2, R'2, and R3. The transmitted signal is illustrated as Rref. FIG. 3 illustrates the summation of the reflected signals in vector form. Each reflected ray defines a vector that varies in amplitude and phase angle depending upon the path length, the number of reflections of the ray, and the distance of penetration through the block. The combination of these vectors forms a summation vector Rsum (or R'sum) that is applied to the mixer 40 along with the reference vector. The output is proportional to the phase angle between the summation and the reference. If the block configuration in the wall is changed, the path length and angle of the summation vector shifts, causing a different voltage output from the mixer. The variation in voltage is sufficient to allow characterization of the block and void configuration within the wall 20'.

Figure 4:
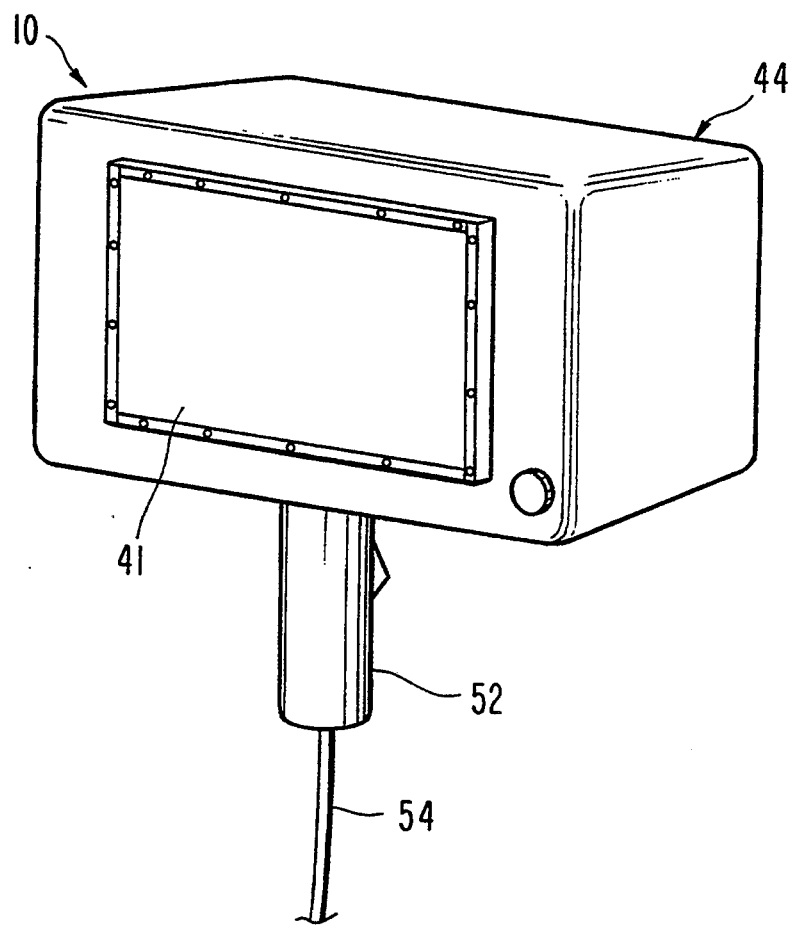
FIG. 4 is a rear perspective view of a portable microwave instrument according to the present invention.
Figure 5:
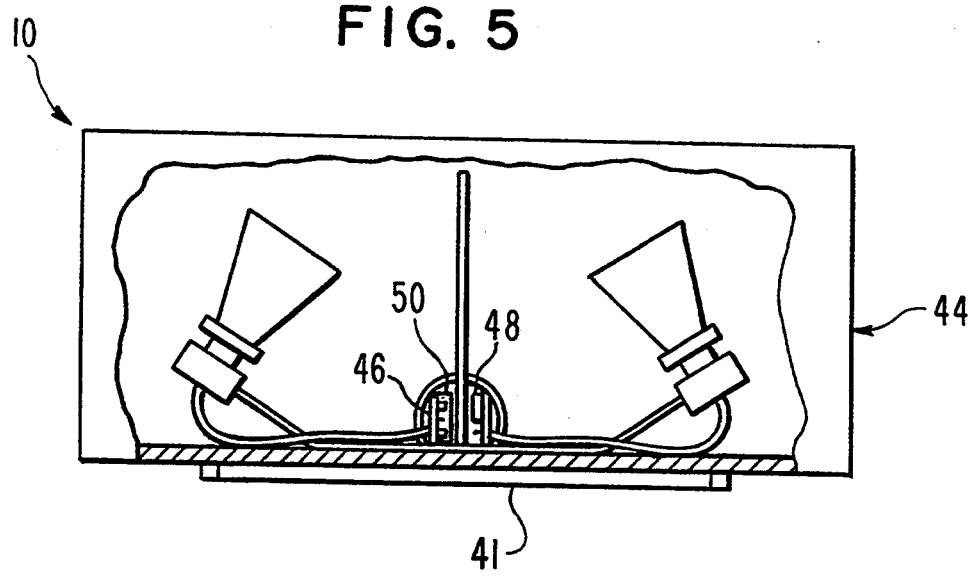
FIG. 5 is a top view, partially cut-away, of the portable microwave instrument of FIG. 4.

Referring to FIGS. 4 and 5, in which the hand-held, portable instrument 10 of the present invention is shown in more detail, a box-shaped housing 44 has an open front through which the transmission and reception of microwave signals is undertaken. A liquid crystal display 41 is mounted on the back of the housing 44 to display a signal indicative of the wall constitution. The voltage signal results from the signal processing circuitry described with respect to FIG. 1 and generally referred to by the numeral 46 in FIG. 5. The voltage signal is applied to a microprocessor 48 which in turn records a two-dimensional signature of the wall for imaging on the display 41. Both the microprocessor 48 and the signal processing circuitry, as well as a battery power supply 50 can be stored in a handle 52 of the instrument 10. Alternatively, the voltage signal can be downloaded to a computer (not shown) through cable 54 for subsequent analysis.

Figure 6:
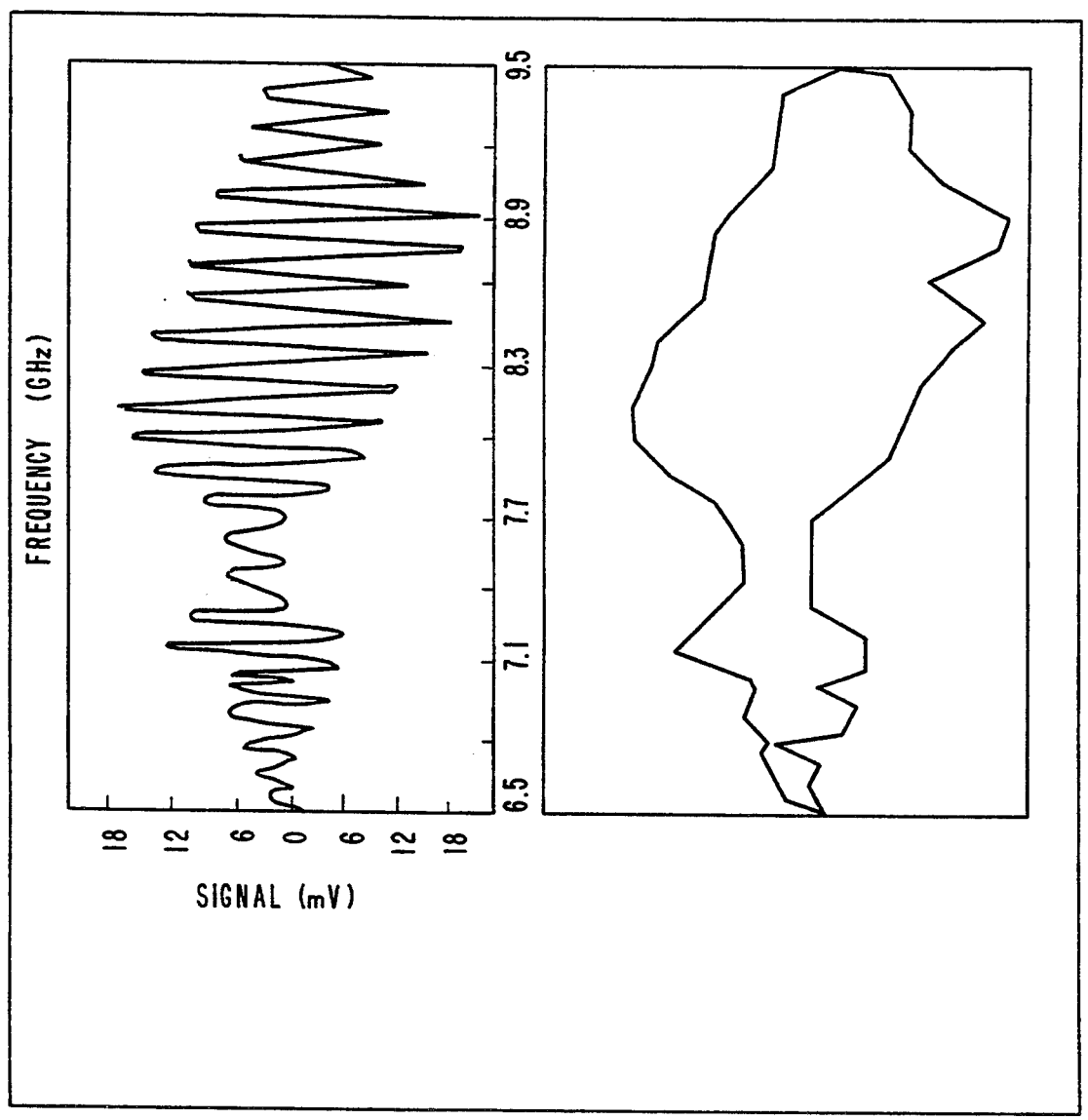
FIG. 6 is a view of the instrument display showing a signal trace of a wall test run and a matched, prerecorded signature envelope.

When conducting an examination of a wall or other support structure, the front of the instrument 10 is positioned by the technician near the wall, the transmission of a microwave signal from the transmitter begins at a given frequency and is then swept through a range of, for example, 7 to 10 GHz. In one particular embodiment, as illustrated in FIG. 6, the center frequency is set at 8.0 GHz, the spread is 1.5 GHz, and the characteristic signature of the signal verses frequency during the sweep is shown in the upper trace. In the lower trace, the outline of a prerecorded wall profile is identified as corresponding to the currently measured wall profile, thus establishing a match. The prerecorded signature is known to have a certain construction, and thus, the previously unknown characteristics of the wall are determined non-destructively.

The microprocessor can be programmed so that when the signature of the test structure matches the standard signature, the structure is considered normal. When the test signature differs from the standard, an anomaly is thereby determined. By varying parameters such as frequency, angle of incidence, or separation between transmitting and receiving horns, the system can be customized for a wide variety of structures.

The microprocessor includes memory for recording signatures of known wall constituents. These known signatures are compared to test signatures for a match.

Thus, by comparing to known signatures, the wall tested can be analyzed for composition.

Once tuned for a particular structure, the instrument 10 eliminates problems of interpretation and allows for rapid evaluation of large areas without the need for highly trained personnel. Moreover, the present invention does not require elaborate surface preparation or the use of special acoustical couplers that are needed with ultrasonics.

While the present invention has been described with respect to the testing of structural members such as walls, it is not limited in this capacity. Preliminary laboratory tests show that the instrument is responsive to physical changes occurring in cement as it cures and may yield early indications of final strength. The instrument also has enough sensitivity to respond to a single sheet of paper behind a thirteen inch block wall, suggesting the ability to detect non-metal pipes or other small anomalies in a wall. Moreover, the instrument could be used to inspect bridges, monitor composites for voids, rebar inspection in concrete, locate buried PVC pipes, measure the flow of fluids in non-metallic pipes, inspect surfaces for absorbed moisture, locate non-metallic land mines in dry sand, and detect motion in adjacent rooms, among other uses.

While advantageous embodiments have been chosen to illustrate the invention, it will be understood by those skilled in the art that various changes and modifications can be made therein without departing from the scope of the invention as defined in the appended claims.

What is claimed is:

1. A portable microwave instrument for evaluating characteristics of a structural member comprising:
    a source of microwave energy;
    a transmitter coupled to the source of microwave energy for transmitting a microwave signal at an angle of incidence into structural member;
    a receiver positioned on the same side of the structural member as the transmitter and being disposed to receive a plurality of reflected microwave signals, each being a partial reflection of the transmitted microwave signal at each boundary between any two constituent materials having different dielectric constants, said reflected signals forming a summation microwave signal received by the receiver; and
    means for determining a phase angle difference between the transmitted microwave signal and the received summation microwave signal, said difference varying in accordance with differences in size, shape and locations of the constituent materials within the structural member.

2. A portable microwave instrument according to claims 1, wherein the determining means includes a signal splitter coupled to the source of microwave energy and having a first signal output delivered to the transmitter and a second signal output delivered to a mixer, along with the reflected summation signal received by the receiver, the mixer having an output indicative of the phase difference between the transmitted microwave signal and the reflected summation signal.

3. A portable microwave instrument according to claim 1, further comprising shield means for segregating desired signal from the direct path between the transmitter and the receiver.

4. A portable microwave instrument according to claim 3, wherein the transmitter and receiver are interconnected in spaced relation to each other, and the shield means comprises a metal shield interposed between the transmitter and receiver to block the direst line-of-site path while permitting a controlled reflected signal.

5. A portable microwave instrument according to claim 2, wherein the second signal output is a reference signal input of the balanced mixer, and the output of the balanced mixer is a voltage that is proportional to the amplitude and phase angle between the reference signal input and the vector sum of the signals reflected from the constituent dielectric materials of the structural member.

6. A portable microwave instrument according to claim 1, further comprising means for displaying the amplitude and phase angle difference.

7. A portable microwave instrument according to claim 6, wherein the display presents relative amplitude and phase of the received signal.

8. A portable microwave instrument according to claim 6, wherein the determining means includes a microprocessor having means for recording two-dimensional signatures corresponding to different configurations of structural members, means for producing a two-dimensional signature of a dielectric structural member being tested, and means for comparing the produced two-dimensional signature to the recorded two-dimensional signatures to determine a match.

9. A portable microwave instrument according to claim 8, wherein the source of microwave energy produces an output signal at a frequency which is swept through a given range during a test procedure to produce a characteristic signature based on a continuum of phase reversals.

10. A portable microwave instrument according to claim 9, wherein the frequency range is between 7 and 10 GHz to cover a range that produces a unique signature of phase reversals for the material being characterized.

11. A method of evaluating characteristics of a structural member comprising:
    transmitting a microwave signal at the structural member at an angle of incidence with a transmitter coupled to a source of microwave energy;
    receiving a plurality of reflected microwave signals with a receiver, each being a partial reflection of the transmitted microwave signal at each boundary between any two constituent materials having different dielectric constants, said reflected signals forming a summation microwave signal received by the receiver, the receiver being positioned on the same side of the structural member as the transmitter; and
    determining phase angle difference between the transmitted microwave signal and the received summation microwave signal, said difference varying in accordance with differences in size, shape and locations of constituent materials within the structural member.

12. A method according to claim 11, wherein the determining step includes splitting an output signal of the source microwave energy with a signal splitter coupled to the source of microwave energy, the splitter having a first signal output to the transmitter and a second signal output, and mixing the second signal output of the signal splitter with the reflected signal received by the receiver with a mixer, the mixer having an output indicative of the phase difference between the first and second inputs.

13. A method according to claim 12, further comprising preventing crosstalk between the transmitter and the receiver, while allowing a signal from the transmitter, through the sample under test, and to the receiver.

14. A method according to claim 13, wherein the step of preventing crosstalk comprises interposing a metal shield between the transmitter and the receiver, positioned so as not to interfere with the intended signal path.

15. A method according to claim 12, wherein the output of the balanced mixer is a voltage that is proportional to the amplitude and phase angle between the reference signal input and the vector sum of the signals reflected from the constituent materials of the structural member.

16. A method according to claim 11, wherein the determining step includes recording two-dimensional signatures corresponding to a continuum of phase reversals created by different configurations of structural members, producing a two-dimensional signature of a structural member being tested, and comparing the produced signature to the recorded signatures to determine a match.

* * * * *